US005762924A

United States Patent [19]

Dall et al.

[11] Patent Number: 5,762,924

[45] Date of Patent: Jun. 9, 1998

[54] RECOMBINANT ENTOMOPOXVIRUS

[75] Inventors: David James Dall, Dickson; Carol Anne Fernon, Page; Alagacone Sriskantha, Florey, all of Australia

[73] Assignee: Commonwealth Scientific and Industrial Research Organisation, Campbell, Australia

[21] Appl. No.: 356,180

[22] PCT Filed: Jun. 15, 1993

[86] PCT No.: PCT/AU93/00284

§ 371 Date: Dec. 16, 1994

§ 102(e) Date: Dec. 16, 1994

[87] PCT Pub. No.: WO93/25666

PCT Pub. Date: Dec. 23, 1993

[30] Foreign Application Priority Data

| | | | |
|---|---|---|---|
| Jun. 16, 1992 | [AU] | Australia | PL 3039 |
| Nov. 19, 1992 | [AU] | Australia | PL 5913 |

[51] Int. Cl.[6] .......... A01N 63/00; C12P 21/00; C12N 15/86; C07H 21/04

[52] U.S. Cl. .......... 424/93.2; 424/93.6; 435/69.1; 435/235.1; 435/320.1; 536/23.72; 536/24.1

[58] Field of Search .......... 435/69.1, 69.3, 435/69.5, 69.6, 172.1, 172.3, 320.1, 235.1; 536/23.1, 23.4, 23.72, 24.1, 24.2; 424/93.2, 93.6

[56] References Cited

FOREIGN PATENT DOCUMENTS

| | | |
|---|---|---|
| 54780/90 | 11/1990 | Australia . |
| 82133/91 | 1/1992 | Australia . |
| 37516/91 | 4/1992 | Australia . |
| 86550/91 | 4/1992 | Australia . |
| 16634/92 | 9/1992 | Australia . |

OTHER PUBLICATIONS

Smith et al., Virology, vol. 123, pp. 393–406, 1982.

"Analysis of Very Late Gene Expression by *Autographa Californica*Nuclear Polyhedrosis Virus and the Further Development of Multiple Expression Vectors", by Ulrike Weyer et al., Journal of General Virology, 71, pp. 1525–1534, 1990.

"Molecular Cloning–A Laboratory Manual", Second Edition, J. Sambrook, E.F. Fritsch, T. Maniatis, Cold Spring Harbor Laboratory Press, 1989, pp. 9.34–9.35, 9.38–9.40, B.25 and, 14.15–14.19.

Malby, R. L. et al., "Recombinant antineuraminidase single chain antibody: Expression, characterization, and crystallization in complex with antigen." *Proteins: Structure, Function, and Genetics*, vol. 16, pp. 57–63, 1993.

Towbin, H. et al., "Electrophoretic transfer of proteins from polyacrylamide gels to nitrocellulose sheets: Procedure and some applications." *Proc. Natl. Acad. Sci. USA*, vol. 76, No. 9, pp. 4350–4354, 1979.

Fernon, C.A. et al., "Replication of *Heliothis armigera* Entomopoxvirus in vitro." In Vitro replication of HaEPV, Mar. 7, 1994, pp. 1–23.

McIntosh, A.H. et al., "Replication and Infectivity of the Single–Embedded Nuclear Polyhedrosis Virus, *Baculovirus heliothis*, in Homologous Cell Lines." *J. Invertebrate Path.*, vol. 37, pp. 258–264, 1981.

Langridge, W.H.R., "Detection of *Amsacta moorei*Entomopoxvirus and Vaccinia Virus Proteins in Cell Cultures Restrictive for Poxvirus Multiplication." *J. Invertebrate Path.*, vol. 42, pp. 77–82, 1983.

Jefferson, R.A. et al., "Gus fusions: β–glucuronidase as a sensitive and versatile gene fusion maker in higher plants." *The EMBO Journal*, vol. 6, No. 13, pp. 3901–3907, 1987.

Smith, D.B. et al., "Single–step purification of polypeptides expressed in *E. coli* as fusions with glutathione S–transferase." *Gene*, vol. 67, pp. 31–40, 1988.

Goodwin, R.H. et al., "Entomopoxvirinae", Atlas of Invertebrate Viruses, J.R. Adams et al. (eds.), Published by CRC press, 1991, pp. 259–285.

Bilimoria, S.L. et al., "Subunit Protein and Alkaline Protease of Entomopoxvirus Spheroids." *Virology*, vol. 96, pp. 596–603, 1979.

Yuen, L. et al., "Identification and Sequencing of the Spheroidin Gene of *Choristoneura biennis* Entomopoxvirus." *Virology*, 175, pp. 427–433, 1990.

Buckner, C.H. et al., "The effect of the poxvirus of the spruce budworm, *Choristoneura fumiferana* (Lipidoptera: Tortricidae), on mammals and birds." *The Canadian Entomologist*, vol. 104, pp. 1333–1342, 1972.

Hall, Richard L. et al., "Identification of an Amsacta Spheroidin–like Protein within the Occlusion Bodies of Choristoneura Entomopoxviruses." *Virology*, vol. 192, pp. 179–187, 1993.

Vialard, J.E. et al., "Identification and Characterization of a Baculovirus Occlusion Body Glycoprotein Which Resembles Spheroidin, an Ectomopoxvirus Protein." *Journal of Virology*, vol. 64, No. 12, pp. 5804–5811, 1990.

Lytvyn, V. et al., "Comparison of the thymidine kinase genes from three entomopoxviruses." *Journal of General Virology*, vol. 73, pp. 3235–3240, 1992.

Hall, Richard L. et al., "Identification, Cloning, and Sequencing of a Fragment of *Amsacta moorei* Entomopoxvirus DNA Containing the Spheroidin Gene and Three Vaccina Virus–Related Open Reading Frames." *Journal of Virology*, vol. 65, No. 12, pp. 6516–6527, 1991.

Erlandson, Martin, "Protease Activity Associated with Occlusion Body Preparations of an Entomopoxvirus from *Melanoplus sanguinipes*." *Journal of Invertebrate Pathology*, vol. 57, pp. 255–263, 1991.

*Primary Examiner*—David Guzo
*Attorney, Agent, or Firm*—Lowe, Price, LeBlanc & Becker

[57] ABSTRACT

Recombinant insect viruses, particularly recombinant *Heliothis armigera* entomopoxvirus (HaEPV) are described wherein heterologous DNA is located in non-essential regions of the viral genome. Such recombinant viruses are useful as biological insecticides and in the production of desired biologically-active proteins, polypeptides and peptides in cell culture.

40 Claims, 11 Drawing Sheets

FIGURE 1(a)

```
1                                                          60
TAATACTCATAGTTAAAATGCAATGTTTTGAAATTTTTATTAAAAAATTAATATAAATGA
(SEQ. ID NO: 1)                                          ---+
                                           (SEQ. ID NO: 2)  M  I
                                              Start p11.5 ORF
```

FIGURE 1(b)

```
61                                                         120
TTATATGCTATATAATTTATGCAATTATTATTATTTGTATAATATTACTTATTAAGTCTA
---------+---------+---------+---------+---------+---------+
 I  C  Y  I  I  Y  A  I  I  I  I  C  I  I  L  L  I  K  S  T
```

FIGURE 1(c)

```
121                                                        180
CAAAAATAAATCAAGATAACCACACTCCCGATCCAGAAAATGAAATTTGTCCTCCGGGAG
---------+---------+---------+---------+---------+---------+
 K  I  N  Q  D  N  H  T  P  D  P  E  N  E  I  C  P  P  G  V
```

FIGURE 1(d)

```
181                                                        240
TATTTGGTAATATACCACATCCATATTATTGCAATAGATTTTATCTTTGCGCCGCCGGAA
---------+---------+---------+---------+---------+---------+
 F  G  N  I  P  H  P  Y  Y  C  N  R  F  Y  L  C  A  A  G  N
```

FIGURE 1(e)

```
241                                                        300
ATGCGATATTACTATTCTGTGCTGAAGGTCATGAATATGATCCTACAATTAGAACATGCG
---------+---------+---------+---------+---------+---------+
 A  I  L  L  F  C  A  E  G  H  E  Y  D  P  T  I  R  T  C  V
```

FIGURE 1(f)

```
301                                                        360
TATTAATATCCGAATATGGATGTACGGCAAACCAAAATAGAAAAAAAAGTAAAAGAAAAT
---------+---------+---------+---------+---------+---------+
  L   I   S   E   Y   G   C   T   A   N   Q   N   R   K   K   S   K   R   K   *
                                                                  End p11.5 ORF
```

FIGURE 1(g)

```
361                                                        420
AATTATTAATTATATCTATGAAAAATAAGTTTTAAAAAATCAAATAAACGAAATAAACCA
--
  I Start intergenic region
```

FIGURE 1(h)

```
421                                                        480
AAATACAAACCAAAGATTAATAATGAATAAATTCTATTATATATGTATTTATATCAATAT
                        ------+---------+---------+---------+
        (SEQ. ID NO: 3)   M   N   K   F   Y   Y   I   C   I   Y   I   N   I
        end intergenic region I Start p50 spindle body protein
```

FIGURE 1(i)

```
481                                                        540
TTTATACGTCTGCGTTAGCGGGCATGGATATATGACATTTCCTATAGCCAGGCAGAGAAG
---------+---------+---------+---------+---------+---------+
  L   Y   V   C   V   S   G   H   G   Y   M   T   F   P   I   A   R   Q   R   R
```

FIGURE 1(j)

```
541                                                        600
ATGTTCGGTAAGGGGAGGTCAGTGGTGGCCACCTAACGGAGATGGAATAACTGATACTAT
---------+---------+---------+---------+---------+---------+
  C   S   V   R   G   G   Q   W   W   P   P   N   G   D   G   I   T   D   T   M
```

FIGURE 1(k)

```
601                                                         660
GTGTAGGGCCGCTTATCAAAATGTATATAATAAAGTATTAAATCAATATAATGACCCACA
---------+---------+---------+---------+---------+---------+
 C  R  A  A  Y  Q  N  V  Y  N  K  V  L  N  Q  Y  N  D  P  Q
```

FIGURE 1(l)

```
661                                                         720
AGAGGCTGCTACTGCTGCTCAATATATGTTCCAACAGGATAATGAATATGCTGCCTTGGC
---------+---------+---------+---------+---------+---------+
 E  A  A  T  A  A  Q  Y  M  F  Q  Q  D  N  E  Y  A  A  L  A
```

FIGURE 1(m)

```
721                                                         780
AGGACCCGATTATACTAATTTATGTAATTTGCAACAAAATGTAGTACCTAACAATTTATG
---------+---------+---------+---------+---------+---------+
 G  P  D  Y  T  N  L  C  N  L  Q  Q  N  V  V  P  N  N  L  C
```

FIGURE 1(n)

```
781                                                         840
CGCCGCGGGAGCCGATGATTGGGATGTAGTTCCATTCGGAGATAAGAGTGGAATGGATTT
---------+---------+---------+---------+---------+---------+
 A  A  G  A  D  D  W  D  V  V  P  F  G  D  K  S  G  M  D  L
```

FIGURE 1(o)

```
841                                                         900
GCCAGGAAATTGGGTACCTACCGTTATTCCTCTTGATAGCAACCACCAATCTAGCGTAGC
---------+---------+---------+---------+---------+---------+
 P  G  N  W  V  P  T  V  I  P  L  D  S  N  H  Q  S  S  V  A
```

FIGURE 1(p)

```
901                                                         960
TCTAGAATTGGAATTTTGTCCTACTGCTGTTCATGATCCTAGCTATTATGAAGTTTATAT
---------+---------+---------+---------+---------+---------+
 L  E  L  E  F  C  P  T  A  V  H  D  P  S  Y  Y  E  V  Y  I
```

FIGURE 1(q)

```
961                                                        1020
CACTAATTCGGGATTTAATGTACATACCGATAATGTAGTATGGGGTAACCTAGAATTGAT
---------+---------+---------+---------+---------+---------+
 T  N  S  G  F  N  V  H  T  D  N  V  V  W  G  N  L  E  L  I
```

FIGURE 1(r)

```
1021                                                       1080
ATTTAATGATACAGTTCCATTAAGACCCAAATCTAGTACTTCGACTTGTAATGCTAATCC
---------+---------+---------+---------+---------+---------+
 F  N  D  T  V  P  L  R  P  K  S  S  T  S  T  C  N  A  N  P
```

FIGURE 1(s)

```
1081                                                       1140
AAACGTTTATAGATTTACAGTATCTATTCCCGTAAGACCTGCTCAATTTGTATTATATGT
---------+---------+---------+---------+---------+---------+
 N  V  Y  R  F  T  V  S  I  P  V  R  P  A  Q  F  V  L  Y  V
```

FIGURE 1(t)

```
1141                                                       1200
AAGATGGCAAAGAATCGATCCCGTCGGTGAAGGATTTTATAATTGTGTTGACATGGCATT
---------+---------+---------+---------+---------+---------+
 R  W  Q  R  I  D  P  V  G  E  G  F  Y  N  C  V  D  M  A  F
```

FIGURE 1(u)

```
1201                                                       1260
CGATTATGCTGCCGGACCTTCCGAAGAAGATGTAATATATCCAGATTACGAGGCTCCTGG
---------+---------+---------+---------+---------+---------+
 D  Y  A  A  G  P  S  E  E  D  V  I  Y  P  D  Y  E  A  P  G
```

FIGURE 1(v)

```
1261                                                       1320
ACAGAATGCATACACTTGTCATGCTAATAGAAATAAATACGGAGGAAATTATGAAAATAC
---------+---------+---------+---------+---------+---------+
 Q  N  A  Y  T  C  H  A  N  R  N  K  Y  G  G  N  Y  E  N  T
```

FIGURE 1(w)

```
1321                                                       1380
TATCGATGAAGATAAATATCAGGCTCAGTTAGATGAATCTATAAAGAGTAGATACGACAA
---------+---------+---------+---------+---------+---------+
 I  D  E  D  K  Y  Q  A  Q  L  D  E  S  I  K  S  R  Y  D  K
```

FIGURE 1(x)

```
1381                                                       1440
ATATAGTAGACATAAAGGAGGAAAATTCGGACAAAAACAATGTAATGGTAATAAACACCA
---------+---------+---------+---------+---------+---------+
 Y  S  R  H  K  G  G  K  F  G  Q  K  Q  C  N  G  N  K  H  H
```

FIGURE 1(y)

```
1441                                                       1500
TTATAATAAATATACCAAATATTATAACCAAAATTATAAAAATAACAAAAATTATTAATT
---------+---------+---------+---------+---------+--------
 Y  N  K  Y  T  K  Y  Y  N  Q  N  Y  K  N  N  K  N  Y  *
                                     end p50 spindle body protein
```

FIGURE 1(z)

```
1501                                                       1560
TCGGGAGTATGGATTATAATACGATCGATAGACACGAGCCAATGATTATTACCAAAGATA
```

FIGURE 2(a)

```
(SEQ. ID NO: 3)  MNKFYYICIYINILYVCVSGHGYMTFPIARQRRCSVRGGQWWPPNGDGIT
                 |||:..|::.  .:.  |  |.:|||||||||||||||.  ||.|:|..|:||
(SEQ. ID NO: 4)  MNKLILISLIASLYQVEVDAHGYMTFPIARQRRCSAAGGNWYPVGGGGIQ
```

FIGURE 2(b)

```
DTMCRAAYQNVYNKVLNQY.NDPQEAATAAQYMFQQDNEYAALAGPDYTN
|.||||||||||:|||||     .|.  :|..||.||: ||||||||||||||||
DPMCRAAYQNVFNKVLNSNGGDVIDASEAANYMYTQDNEYAALAGPDYTN
```

FIGURE 2(c)

```
LCNLQQNVVPNNLCAAGADDWDVVPFGDKSGMDLPGNWVPTVIPLDSNHQ
:|::||.|||.  ||||||.||.:  ||||||||||||.|.||:|.|..|:|
ICHIQQRVVPSYLCAAGASDWSIRPFGDKSGMDLPGSWTPTIIQLSDNQQ
```

FIGURE 2(d)

```
SSVALELEFCPTAVHDPSYYEVYITNSGFNVHTDNVVWGNLELIFNDTVP
|.|.:|||||||||||||||||||||||.:|||.||||||:||:||:|:||.
SNVVMELEFCPTAVHDPSYYEVYITNPSFNVYTDNVVWANLDLIYNNTVT
```

FIGURE 2(e)

```
         .         .         .         .         .
LRPKSSTSTCNANPNVYRFTVSIPVRPAQFVLYVRWQRIDPVGEGFYNCV
|||| ..|||.||. ||||.|||||||.||||||||||||||||||||||
LRPKLPESTCAANSMVYRFEVSIPVRPSQFVLYVRWQRIDPVGEGFYNCV
```

FIGURE 2(f)

```
         .         .         .         .         .
DMAFDYAAGPSEEDVIYPDYEAPGQNAYTCHANRNKYGGNYENTIDEDKY
|| |.|..||.|||:| |:||  .:|. .| | | ..|.   |.::|:||
DMKFKYSEGPDEEDIIEPEYE..VDNEAECFAYRTNSGNVNVNPLQENKY
```

FIGURE 2(g)

```
         .         .         .         .         .
QAQLDESIKSRYDKYSRHKGGKFGQKQCNGNKHHYNKYTKYYNQNYKNNK
 |  :..|:    ... |..|      |. |::: |.|.|||...|. |.
MAYANKAIR....NINTHSNG......CSRNRNNKNNYNKYYSKTYNYNQ
```

FIGURE 2(h)

```
NY*
|
NRK*
```

FIGURE 3(a)

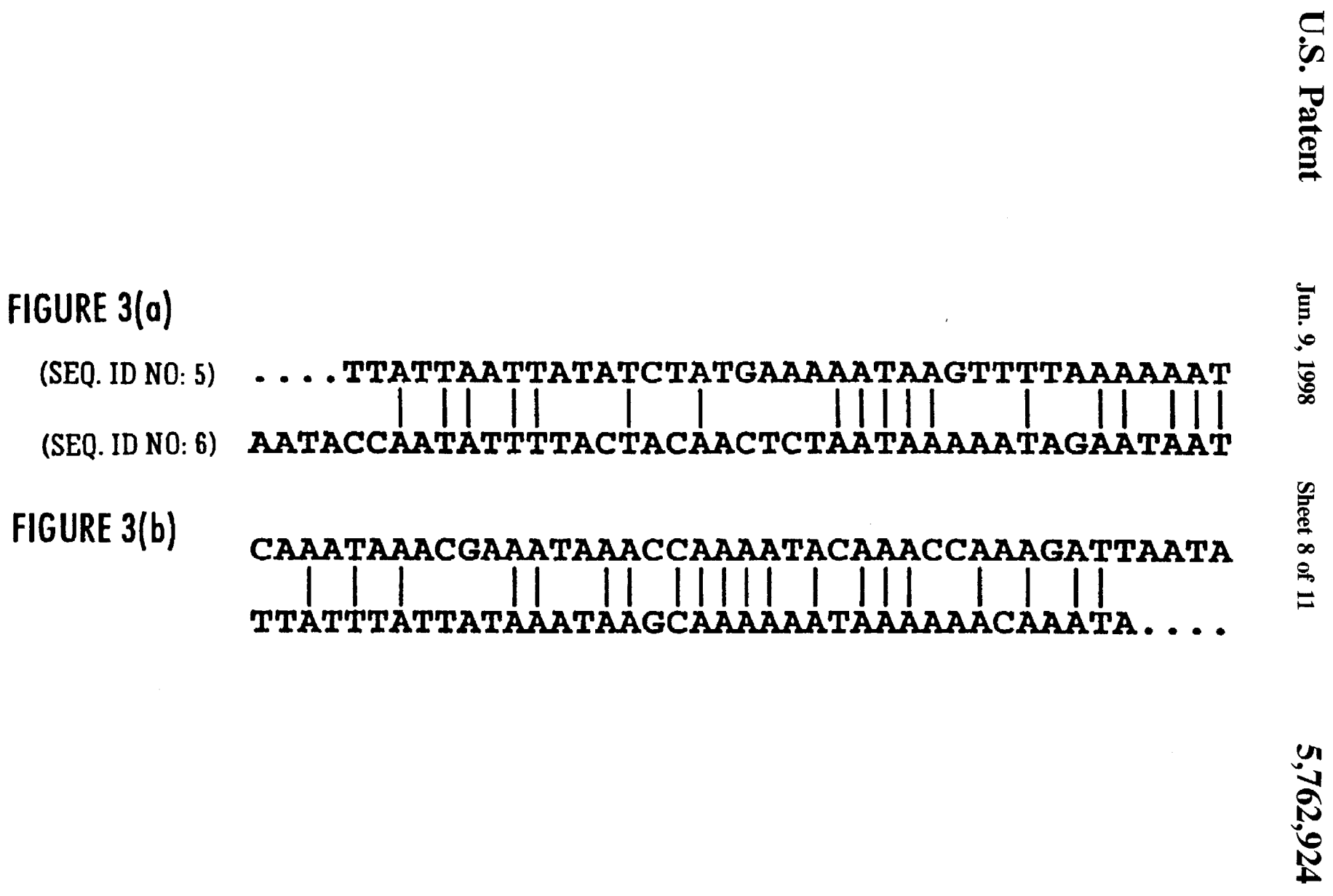

(SEQ. ID NO: 5) ....TTATTAATTATATCTATGAAAAATAAGTTTTAAAAAAT (SEQ. ID NO: 6) AATACCAATATTTTACTACAACTCTAATAAAAATAGAATAAT

FIGURE 3(b)

CAAATAAACGAAATAAACCAAAATACAAACCAAAGATTAATA

TTATTTATTATAAATAAGCAAAAAATAAAAAACAAATA....

SEQUENCE LISTING ( 1 ) GENERAL INFORMATION:

( i i i ) NUMBER OF SEQUENCES: 11

( 2 ) INFORMATION FOR SEQ ID NO:1:

( i ) SEQUENCE CHARACTERISTICS:
( A ) LENGTH: 1560 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:1:

-continued

TAATACTCAT AGTTAAAATG CAATGTTTTG AAATTTTTAT TAAAAAATTA ATATAAATGA 60

TTATATGCTA TATAATTTAT GCAATTATTA TTATTTGTAT AATATTACTT ATTAAGTCTA 120

CAAAAATAAA TCAAGATAAC CACACTCCCG ATCCAGAAAA TGAAATTTGT CCTCCGGGAG 180

TATTTGGTAA TATACCACAT CCATATTATT GCAATAGATT TTATCTTTGC GCCGCCGGAA 240

ATGCGATATT ACTATTCTGT GCTGAAGGTC ATGAATATGA TCCTACAATT AGAACATGCG 300

TATTAATATC CGAATATGGA TGTACGGCAA ACCAAAATAG AAAAAAAAGT AAAAGAAAAT 360

AATTATTAAT TATATCTATG AAAAATAAGT TTTAAAAAAT CAAATAAACG AAATAAACCA 420

AAATACAAAC CAAAGATTAA TAATGAATAA ATTCTATTAT ATATGTATTT ATATCAATAT 480

TTTATACGTC TGCGTTAGCG GGCATGGATA TATGACATTT CCTATAGCCA GGCAGAGAAG 540

ATGTTCGGTA AGGGGAGGTC AGTGGTGGCC ACCTAACGGA GATGGAATAA CTGATACTAT 600

GTGTAGGGCC GCTTATCAAA ATGTATATAA TAAAGTATTA AATCAATATA ATGACCCACA 660

AGAGGCTGCT ACTGCTGCTC AATATATGTT CCAACAGGAT AATGAATATG CTGCCTTGGC 720

AGGACCCGAT TATACTAATT TATGTAATTT GCAACAAAAT GTAGTACCTA ACAATTTATG 780

CGCCGCGGGA GCCGATGATT GGGATGTAGT TCCATTCGGA GATAAGAGTG GAATGGATTT 840

GCCAGGAAAT TGGGTACCTA CCGTTATTCC TCTTGATAGC AACCACCAAT CTAGCGTAGC 900

TCTAGAATTG GAATTTTGTC CTACTGCTGT TCATGATCCT AGCTATTATG AAGTTTATAT 960

CACTAATTCG GGATTTAATG TACATACCGA TAATGTAGTA TGGGGTAACC TAGAATTGAT 1020

ATTTAATGAT ACAGTTCCAT TAAGACCCAA ATCTAGTACT TCGACTTGTA ATGCTAATCC 1080

AAACGTTTAT AGATTTACAG TATCTATTCC CGTAAGACCT GCTCAATTTG TATTATATGT 1140

AAGATGGCAA AGAATCGATC CCGTCGGTGA AGGATTTTAT AATTGTGTTG ACATGGCATT 1200

CGATTATGCT GCCGGACCTT CCGAAGAAGA TGTAATATAT CCAGATTACG AGGCTCCTGG 1260

ACAGAATGCA TACACTTGTC ATGCTAATAG AAATAAATAC GGAGGAAATT ATGAAAAATAC 1320

TATCGATGAA GATAAATATC AGGCTCAGTT AGATGAATCT ATAAAGAGTA GATACGACAA 1380

ATATAGTAGA CATAAAGGAG GAAAATTCGG ACAAAAACAA TGTAATGGTA ATAAACACCA 1440

TTATAATAAA TATACCAAAT ATTATAACCA AAATTATAAA AATAACAAAA ATTATTAATT 1500

TCGGGAGTAT GGATTATAAT ACGATCGATA GACACGAGCC AATGATTATT ACCAAAGATA 1560

( 2 ) INFORMATION FOR SEQ ID NO:2:

( i ) SEQUENCE CHARACTERISTICS:
( A ) LENGTH: 101 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:2:

Met Ile Ile Cys Tyr Ile Ile Tyr Ala Ile Ile Ile Ile Cys Ile Ile
1 5 10 15

Leu Leu Ile Lys Ser Thr Lys Ile Asn Gln Asp Asn His Thr Pro Asp
20 25 30

Pro Glu Asn Glu Ile Cys Pro Pro Gly Val Phe Gly Asn Ile Pro His
35 40 45

Pro Tyr Tyr Cys Asn Arg Phe Tyr Leu Cys Ala Ala Gly Asn Ala Ile
50 55 60

Leu Leu Phe Cys Ala Glu Gly His Glu Tyr Asp Pro Thr Ile Arg Thr
65 70 75 80

-continued

Cys Val Leu Ile Ser Glu Tyr Gly Cys Thr Ala Asn Gln Asn Arg Lys
85 90 95

Lys Ser Lys Arg Lys
100

( 2 ) INFORMATION FOR SEQ ID NO:3:

( i ) SEQUENCE CHARACTERISTICS:
( A ) LENGTH: 331 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:3:

Met Asn Lys Phe Tyr Tyr Ile Cys Ile Tyr Ile Asn Ile Leu Tyr Val
1 5 10 15

Cys Val Ser Gly His Gly Tyr Met Thr Phe Pro Ile Ala Arg Gln Thr
20 25 30

Met Cys Arg Ala Ala Tyr Gln Asn Val Tyr Asn Lys Val Leu Asn Gln
35 40 45

Tyr Asn Asp Pro Gln Glu Ala Ala Thr Ala Ala Gln Tyr Met Phe Gln
50 55 60

Gln Asp Asn Glu Tyr Ala Ala Leu Ala Gly Pro Asp Tyr Thr Asn Leu
65 70 75 80

Cys Asn Leu Gln Gln Asn Val Val Pro Asn Asn Leu Cys Ala Ala Gly
85 90 95

Ala Asp Asp Trp Asp Val Val Pro Phe Gly Asp Lys Ser Gly Met Asp
100 105 110

Leu Pro Gly Asn Trp Val Pro Thr Val Ile Pro Leu Asp Ser Asn His
115 120 125

Gln Ser Ser Val Ala Leu Glu Leu Glu Phe Cys Pro Thr Ala Val His
130 135 140

Asp Pro Ser Tyr Tyr Glu Val Tyr Ile Thr Asn Ser Gly Phe Asn Val
145 150 155 160

His Thr Asp Asn Val Val Trp Gly Asn Leu Glu Leu Ile Phe Asn Asp
165 170 175

Thr Val Pro Leu Arg Pro Lys Ser Ser Thr Ser Thr Cys Asn Ala Asn
180 185 190

Pro Asn Val Tyr Arg Phe Thr Val Ser Ile Pro Val Arg Pro Ala Gln
195 200 205

Phe Val Leu Tyr Val Arg Trp Gln Arg Ile Asp Pro Val Gly Glu Gly
210 215 220

Phe Tyr Asn Cys Val Asp Met Ala Phe Asp Tyr Ala Ala Gly Pro Ser
225 230 235 240

Glu Glu Asp Val Ile Tyr Pro Asp Tyr Glu Ala Pro Gly Gln Asn Ala
245 250 255

Tyr Thr Cys His Ala Asn Arg Asn Lys Tyr Gly Gly Asn Tyr Glu Asn
260 265 270

Thr Ile Asp Glu Asp Lys Tyr Gln Ala Gln Leu Asp Glu Ser Ile Lys
275 280 285

Ser Arg Tyr Asp Lys Tyr Ser Arg His Lys Gly Gly Lys Phe Gly Gln
290 295 300

Lys Gln Cys Asn Gly Asn Lys His His Tyr Asn Lys Tyr Thr Lys Tyr
305 310 315 320

-continued

Tyr Asn Gln Asn Tyr Lys Asn Asn Lys Asn Tyr
325 330

( 2 ) INFORMATION FOR SEQ ID NO:4:

( i ) SEQUENCE CHARACTERISTICS:
( A ) LENGTH: 341 amino acids
( B ) TYPE: amino acid
( C ) STRANDEDNESS: single
( D ) TOPOLOGY: linear ( i i ) MOLECULE TYPE: peptide ( i i i ) HYPOTHETICAL: NO ( i v ) ANTI-SENSE: NO ( x i ) SEQUENCE DESCRIPTION: SEQ ID NO:4:

Met Asn Lys Leu Ile Leu Ile Ser Leu Ile Ala Ser Lys Tyr Gln Val
1 5 10 15

Glu Val Asp Ala His Gly Tyr Met Thr Phe Pro Ile Ala Arg Gln Arg
20 25 30

Arg Cys Ser Ala Ala Gly Gly Asn Trp Tyr Pro Val Gly Gly Gly Gly
35 40 45

Ile Gln Asp Pro Met Cys Arg Ala Ala Tyr Gln Asn Val Phe Asn Lys
50 55 60

Val Leu Asn Ser Asn Gly Gly Asp Val Ile Asp Ala Ser Glu Ala Ala
65 70 75 80

Asn Tyr Met Tyr Thr Gln Asp Asn Glu Tyr Ala Ala Leu Ala Gly Pro
85 90 95

Asp Tyr Thr Asn Ile Cys His Ile Gln Gln Arg Val Val Pro Ser Tyr
100 105 110

Leu Cys Ala Ala Gly Ala Ser Asp Trp Ser Ile Arg Pro Phe Gly Asp
115 120 125

Lys Ser Gly Met Asp Leu Pro Gly Ser Trp Thr Pro Thr Ile Ile Gln
130 135 140

Leu Ser Asp Asn Gln Gln Ser Asn Val Val Met Glu Leu Glu Phe Cys
145 150 155 160

Pro Thr Ala Val His Asp Pro Ser Tyr Tyr Glu Val Tyr Ile Thr Asn
165 170 175

Pro Ser Phe Asn Val Tyr Thr Asp Asn Val Val Trp Ala Asn Leu Asp
180 185 190

Leu Ile Tyr Asn Asn Thr Val Thr Leu Arg Pro Lys Leu Pro Glu Ser
195 200 205

Thr Cys Ala Ala Asn Ser Met Val Tyr Arg Phe Glu Val Ser Ile Pro
210 215 220

Val Arg Pro Ser Gln Phe Val Leu Tyr Val Arg Trp Gln Arg Ile Asp
225 230 235 240

Pro Val Gly Glu Gly Phe Tyr Asn Cys Val Asp Met Lys Phe Lys Tyr
245 250 255

Ser Glu Gly Pro Asp Glu Glu Asp Ile Ile Glu Pro Glu Tyr Glu Val
260 265 270

Asp Asn Glu Ala Glu Cys Phe Ala Tyr Arg Thr Asn Ser Gly Asn Val
275 280 285

Asn Val Asn Pro Leu Gln Glu Asn Lys Tyr Met Ala Tyr Ala Asn Lys
290 295 300

Ala Ile Arg Asn Ile Asn Thr His Ser Asn Gly Cys Ser Arg Asn Arg
305 310 315 320

-continued

Asn Asn Lys Asn Asn Tyr Asn Lys Tyr Tyr Ser Lys Thr Tyr Asn Tyr
325 330 335

Asn Gln Asn Arg Lys
340

( 2 ) INFORMATION FOR SEQ ID NO:5:

( i ) SEQUENCE CHARACTERISTICS:
( A ) LENGTH: 80 base pairs
( B ) TYPE: nucleic acid
( C ) STRANDEDNESS: single
( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:5:

TTATTAATTA TATCTATGAA AAATAAGTTT TAAAAAATCA AATAAACGAA ATAAACCAAA 60

ATACAAACCA AAGATTAATA 80

( 2 ) INFORMATION FOR SEQ ID NO:6:

( i ) SEQUENCE CHARACTERISTICS:
( A ) LENGTH: 80 base pairs
( B ) TYPE: nucleic acid
( C ) STRANDEDNESS: single
( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:6:

AATACCAATA TTTTACTACA ACTCTAATAA AAATAGAATA ATTTATTTAT TATAAATAAG 60

CAAAAAATAA AAAACAAATA 80

( 2 ) INFORMATION FOR SEQ ID NO:7:

( i ) SEQUENCE CHARACTERISTICS:
( A ) LENGTH: 11 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:7:

His Gly Tyr Met Thr Phe Pro Ile Ile Ala Gln
1 5 10

( 2 ) INFORMATION FOR SEQ ID NO:8:

( i ) SEQUENCE CHARACTERISTICS:
( A ) LENGTH: 11 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:8:

His Gly Tyr Met Thr Phe Pro Ile Ala Ala Gln
1 5 10

-continued ( 2 ) INFORMATION FOR SEQ ID NO:9:

( i ) SEQUENCE CHARACTERISTICS:
( A ) LENGTH: 23 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:9:

GAATATGCNG CNTTAGCAGG NCC 23

( 2 ) INFORMATION FOR SEQ ID NO:10:

( i ) SEQUENCE CHARACTERISTICS:
( A ) LENGTH: 23 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:10:

ACANTTNTAN AANCCTCNCC NAC 23

( 2 ) INFORMATION FOR SEQ ID NO:11:

( i ) SEQUENCE CHARACTERISTICS:
( A ) LENGTH: 22 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:11:

GATCTTAAAT AGATCTATTT AA 22

RECOMBINANT ENTOMOPOXVIRUS

This application is a 371 of PCT/AU93/00284, filed Jun. 15, 1993.

This invention relates to the production of recombinant entomopoxviruses (EPV's), particularly recombinant *Heliothis armigera* entomopoxviruses (HaEPV's), capable of expressing heterologous DNA sequences. Particular applications of the invention include the use of the recombinant entomopoxviruses as biological insecticides and in the production of desired, biologically-active proteins, polypeptides and peptides in cell culture.

Entomopoxviruses are large, double-stranded DNA viruses of insects, and have to date been described from species of caterpillars, beetles and locusts (Goodwin et al., 1991). The economic importance of these insect groups has led to serious consideration of EPV's as potential biological control agents, and investigation by others has documented various characteristics which support their use in this capacity. For example, while the collective EPV host range is broad, covering the important insect groups, individual EPV isolates generally have a narrow host range, allowing potentially high levels of control specificity. Additionally, vertebrates (and vertebrate cell cultures) exposed to large amounts of infectious EPV have shown no sign of infection or other discernible ill-effect (Buckner & Cunningham, 1972; Langridge, 1973).

These factors confer significant potential for the use of EPV's as insect control agents. Unfortunately however, most EPV's exhibit low levels of pathogenicity. This trait, which has prevented serious attempts to develop the viruses as major commercial insecticides, may be overcome, conceivably, by the production of recombinant entomopoxviruses capable of expressing heterologous DNA sequences encoding agents toxic or otherwise deleterious to insects.

Recombinant entomopoxviruses also hold great potential for the production of homogenous and biologically active proteins, polypeptides and peptides. Such products are presently generated either from recombinant bacteria or through the use of expression vectors in eukaryotic cells. The first method is technically more simple, but suffers from the drawback that many proteins of eukaryote origin are not correctly processed in bacteria. Without correct processing many proteins are biologically inactive, and thus of little use or value. On the other hand, production from expression vectors in vertebrate cells is traditionally more expensive, with smaller yields of protein. Some eukaryotic expression vectors (e.g. baculoviruses) also cause lysis of the host cell.

In contrast to the baculoviruses, EPV's do not necessarily cause lysis of the infected cell, thereby offering potential for long term persistent infection of large scale cell culture. This should permit enhanced production efficiency of proteins, especially of those which are secreted from the host cell, since collection of the product (via periodic removal of cell culture medium) will not require destruction of the cells.

Thus it is an object of the present invention to provide recombinant entomopoxviruses suitable for use as biological insecticides and/or as expression vectors for the production of desired proteins, polypeptides and peptides in cell culture systems. To achieve this object it is necessary that non-essential regions are identified in the genomes of EPV's. The identification of such regions would provide sites which could be utilised for development of an EPV viral vector, with heterologous DNA inserted into the non-essential region of the EPV genome by any of the methods known in the art (but most conveniently, homologous recombination), optionally with deletion of the non-essential region or portion thereof prior to insertion of the foreign DNA.

The spheroidin protein of EPV is a major component of the occlusion body (spheroid). Since occlusion is only required for horizontal virus transmission, and not infection, the single spheroidin gene driven by a strong promoter provides a very attractive site for the insertion of heterologous sequences into the EPV genome. The sequence of the gene which encodes *Amsacta moorei* EPV (AmEPV) spheroidin has now been reported (Hall and Moyer, 1991). Its product is a 115 kDa protein with a high cysteine content, and a large number of potential glycosylation sites. This protein is unrelated to others previously described, including the major protein component of purified preparations of *Choristoneura biennis* EPV (CbEPV), which has previously been identified as the spheroidin moiety of that virus (Yuen et al. 1990).

It has now been found that entomopoxviruses possess alternative, non-essential regions within their genomes which are suitable for use as sites for the introduction of heterologous DNA.

Accordingly, in one aspect of the present invention, there is provided a recombinant entomopoxvirus, characterised in that heterologous DNA is located in one or more of the following regions of the entomopoxvirus genome:

(i) p11.5 open reading frame (ORF) region;

(ii) thymidine kinase (TK) encoding region;

(iii) spindle protein encoding region;

(iv) an intergenic region.

By intergenic region it is meant any region of the viral genome which follows the first translation termination codon of an upstream gene or open reading frame (ORF) actually or potentially encoding a viral protein, and which precedes the translation initiation codon of the following downstream gene or ORF. As such the intergenic region may contain enhancer and promoter elements, other functional elements, and other nucleotide sequences which lack identified activity.

Preferably, the heterologous DNA is inserted into the p11.5 ORF region or the spindle protein encoding region.

Preferably the recombinant entomopoxvirus is *Amsacta moorei* EPV, *Choristoneura biennis* EPV, *Heliothis armigera* EPV, *Choristoneura fumiferana* EPV, *Aphodius tasmaniae* EPV, *Dermolepida albohirtum* EPV, *Melolontha melolontha* EPV or *Servicesthis nigrolineata* EPV.

In addition to spheroids, many EPV isolates also produce large numbers of a second type of proteinaceous structure known as a spindle body. These bodies do not occlude virus particles and in some EPV's they are themselves occluded into the matrix of the spheroid. The spindle protein (fusolin) encoding region (and adjacent regions) have been isolated from *Heliothis armigera* EPV (HaEPV), and the sequence is provided at FIG. 1. Thus, in a second aspect, the invention provides an isolated DNA molecule comprising the sequence for an EPV spindle protein or a portion thereof, optionally together with the 5' promoter sequence.

The p11.5 ORF and the adjacent 5' regions have also been isolated from HaEPV. The sequence of these regions is provided at FIG. 1. Accordingly, in a third aspect, the invention provides an isolated DNA molecule comprising the sequence for p11.5 ORF or a portion thereof, optionally together with the 5' promoter/intergenic sequence.

In a further aspect, the invention provides a recombinant HaEPV, characterised in that heterologous DNA is located in one or more non-essential regions of the genome. Preferably, the heterologous DNA is inserted into one or more of the following regions of the entomopoxvirus genome:

(i) p11.5 open reading frame (ORF) region;

(ii) thymidine kinase (TK) encoding region;

(iii) spindle protein encoding region;

(iv) spheroidin encoding region;

(v) an intergenic region.

More preferably, the heterologous DNA is inserted into the p11.5 ORF region or the spindle protein encoding region.

Recombinant entomopoxviruses according to the invention may be used as biological insecticides, optionally in admixture with an acceptable agricultural carrier. The heterologous DNA inserted into the genome of the recombinant EPV may comprise genes encoding one or more substances that are deleterious to insects. Such substances include, for example, *Bacillus thuringiensis* δ-toxin, insect neurohormones or proteins which interact with such hormones (e.g. juvenile hormone esterase), insecticidal compounds from wasp, scorpion venom or other heterologous origin, or factors designed to attack and kill infected cells in such a way as to cause pathogenesis in the infected tissue (e.g. a ribozyme targeted against an essential cellular function). Expression of the heterologous genes may be driven by the natural or other suitable promoter, but more preferably by an entomopoxvirus promoter, particularly the spindle protein gene promoter, the spheroidin gene promoter or the p11.5 ORF promoter. Thus, in a further aspect the present invention comprises an isolated DNA molecule comprising the promoter region, or a portion thereof, derived from the spheroidin gene or spindle protein gene of an entomopoxvirus or the p11.5 ORF of an insect virus, preferably an entomopoxvirus.

Further, the recombinant entomopoxviruses according to the invention may be used for the production of desired, biologically-active proteins, polypeptides or peptides, for example cytokines such an interferons (e.g. IFN-α, IFN-β, IFN-γ), tissue plasminogen activator (TPA), lymphotoxin (LT), macrophage activating factor (MAP), insulin, epithelial cell growth factor (EGF), human growth hormone (hGH), antibodies and fragments thereof, etc. Expression of the gene encoding the desired product may be driven by the gene's natural promoter or another suitable promoter, but more preferably expression is driven by an entomopoxvirus promoter, particularly the spindle protein gene promoter, the spheroidin gene promoter or the p11.5 ORF promoter. Recombinant HaEPV's may be used to produce desired proteins, polypeptides and peptides by infecting cultured Helicoverpa or Spodoptera cells, for example, cells comprising or derived from the Helicovexpa BCIRL-HZ-AM1 line (U.S. Dept. of Agriculture), the Spodoptera Sf9 line (American Type Culture Collection), or similar cells.

The p11.5 ORF also appears to be both present and expressed in nuclear polyhedrosis viruses (NPV's). That is, GeneBank Accession M59422, locus NPAIEN, describes a 2011 bp ds-DNA from AcNPV which contains a previously undescribed ORF potentially encoding an HaEPV p11.5 homologue. The ORF is in reverse orientation, as published, beginning (i.e. 3' end of gene) at nucleotide position 1662. Using an AcNPV PCR-derived amplicon spanning positions 1662 to 1969 as template for a random primed labelled probe, Northern blots from AcNPV-infected and healthy Spodoptera Sf9 cells indicate that an RNA product of a size expected to encode the p11.5 protein homologue (about 300 nucleotides) is present in infected, but not healthy cells. This strongly suggests that the ORF is in fact a functional AcNPV gene. Expression of the AcNPV gene appears to peak about 48 hours post-infection.

Further, GeneBank Accession M63414, locus NPOIE1A, describes a 3792 bp ds-DNA sequence from *Orgia pseudotsugata* NPV (OpNPV) which also contains a previously undescribed ORF potentially encoding a p11.5 homologue. The region of homology extends from published base 350 (5' end of the putative gene) to base 637, which is the last base of the putative translation termination codon.

Thus, in a still further aspect, the invention provides a recombinant NPV, characterised in that heterologous DNA is located in a region of the NPV genome substantially homologous to the p11.5 ORF entomopoxvirus region.

Preferably the NPV is a baculovirus, particularly AcNPV or OpNPV. The heterologous DNA may be of the kinds described above.

Thus, the invention should also be understood to extend to methods for producing desired proteins, polypeptides or peptides, comprising infecting susceptible host cells with a recombinant entomopoxvirus or recombinant nuclear polyhedrosis virus according to the present invention.

Recombinant HaEPV's may be used for the control of, for example, Heliothis/Helicovezpa species and Spodoptera species. Recombinant NPV's may be used for the control of, for example, various Lepidopterans. Thus, the invention also extends to methods for controlling the proliferation of pest insects, comprising applying to an infested area a recombinant entomopoxvirus or recombinant nuclear polyhedrosis virus according to the present invention, optionally in admixture with a suitable carrier.

As mentioned above, the heterologous DNA is most conveniently inserted into the non-essential region of the EPV or NPV genome by homologous recombination. Conceivably, homologous recombination may be achieved by using a construct wherein the heterologous DNA is flanked by a sequence of 5–10 nucleotide bases corresponding to the target, non-essential region. However, flanking sequences of 0.5–2.0 kb should provide desired recombinants with greater efficiency.

The invention will now be further described by way of the accompanying figures and the following non-limiting examples.

BRIEF DESCRIPTION OF THE FIGURES

FIGS. 1(*a*)–1(z) shows the genomic DNA sequence (SEQ ID NO:1) of *Heliothis armigera* entomopoxvirus p11.5 ORF, p50 spindle protein (fusolin), intergenic and flanking regions. The sequence is from the BglII 4.9 Kb clone 36.

FIGS. 2(*a*)–2(*h*) compares the amino acid sequences of *Heliothis armigera* entomopoxvirus p50 spindle protein (top sequence, SEQ ID NO:3) with the homologous protein from *Choristoneura biennis* entomopoxvirus (bottom sequence, SEQ ID NO:4). Single letter amino acid code used throughout.

FIGS. 3(*a*) and 3(*b*) compares the nucleotide sequence of the *Heliothis armigera* entomopoxvirus intergenic region between p11.5 ORF and p50 spindle protein (top sequence, SEQ ID NO:5) with the nucleotide sequence immediately upstream of the homologous gene in *Choristoneura biennis* entomopoxvirus (bottom sequence, SEQ ID NO:6).

(B): Demonstration of GUS activity in *H. zea* cells infected with wild-type HaEPV (left) or $G^+F^-$ recombinant HaEPVs derived from pEPAS3:GUS (right).

In each case it is clear that GUS activity is absent in cells infected with wild-type HaEPV, but present in those infected with recombinant HaEPV.

Figure 5:
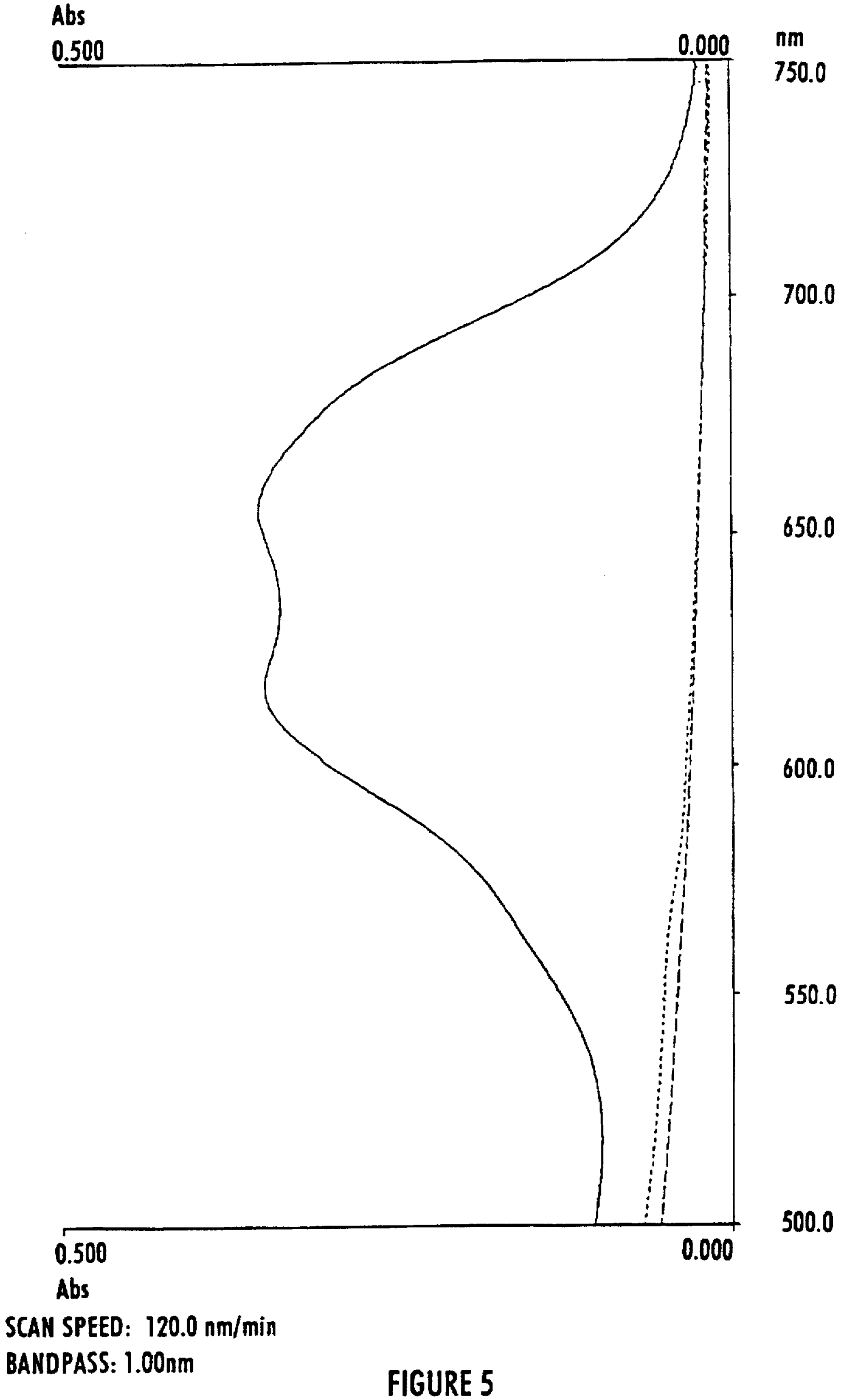

FIG. 5 provides a spectrophotometric analysis of lysates from cell cultures infected with GUS-expressing recombinant *Heliothis armigera* entomopoxvirus (HaEPV) clone H12 (solid line), wild-type HaEPV (dotted line) and mock-infected (dashed line). The absorption peak from GUS-expressing recombinant indicates the presence of GUS-catalysed reaction product.

Figure 6:
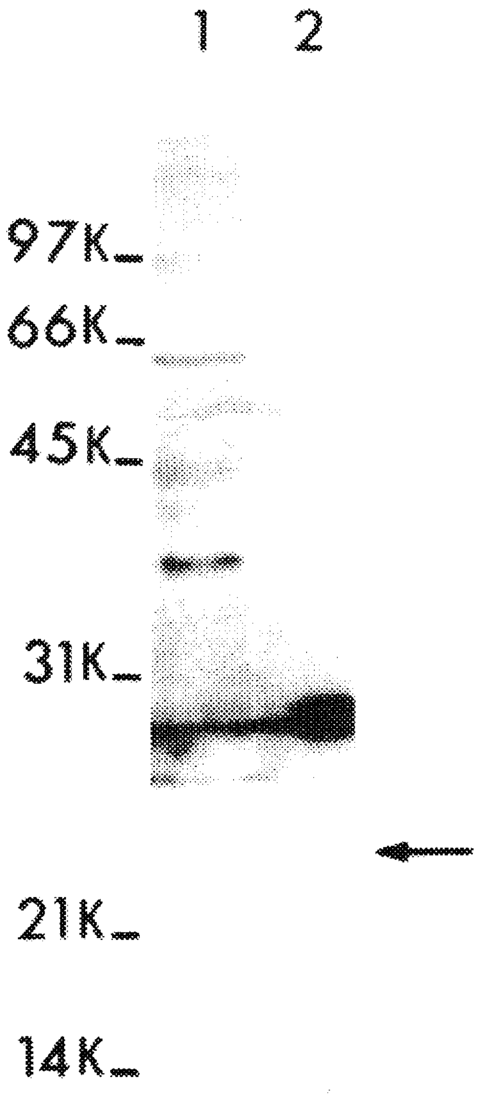

FIG. 6 Expression of the NC10 protein by recombinant *Heliothis armigera* entomopoxvirus (HaEPV). The figure shows a western blot of lysate of *H. zea* cells infected with a mixture os wild-type and NC10-expressing recombinant HaEPV's (lane 1), or with wild-type HaEPV only (lane 2). Arrow points to expected migration position of NC10 monomer in *H. zea* cell lysates; note presence of immunoreactive band at this position in lane 1, and failure to detect this band in lane 2. Numbers on left of figure show migration positions and molecular weights of protein markers.

EXAMPLE 1

Characterisation of *Heliothis armigera* entomopoxvirus genes and viral proteins Virus. Wild-type *Heliothis armigera* entomopoxvirus (HaEPV) was obtained from Dr. R. E. Teakle (Entomology Branch, Queensland Department of Primary Industries) and propagated in laboratory strains of *Helicoverpa armigera* derived from field collected insects (Fernon et al., in preparation).

Spheroids and associated spindle bodies were purified from macerated infected larvae by differential contrifugation. Purification of virions essentially followed the method of Arif (1976); virions were released from spheroids by dissociation with sodium thioglycollate in carbonate buffer, centrifuged on 40–60% sucrose gradients in 1 mM Tris pH 8.0 and dialysed against 2 mM MOPS, pH 7.1.

Viral genomic DNA was purified from virions by incubation in 1 mg/ml protease K (room temperature overnight, then 2 h at 37°), extraction in TE-saturated (10 mM Tris, pH 8.0, 1 mM EDTA) phenol/chloroform/isoamyl alcohol (25:24:1 respectively), and precipitation.

Protein Analysis. HaEPV spheroids and spindle bodies were solublised using the method described by Erlandson (1991), in the buffer described by Bilimoria and Arif (1979), except that final concentrations were 6.4M urea, 4% SDS and 4% mercaptoethanol. Proteins were separated by SDS-PAGE and stained with colloidal Coomassie Blue (Gradipore Australia). In some cases Laemmli gels were pre-run for 30 mins with 20 mM glutathione in the upper chamber running buffer; that buffer was discarded and replaced with standard running buffer prior to sample loading. Western blotting onto nitrocellulose membrane essentially followed the method of Towbin et al. (1979). Testing for glycosylation of denatured viral proteins blotted on nitrocellulose membrane employed a glycan detection kit (Boehringer Mannheim) used in accordance with manufacturer's instructions. Blotting of proteins onto PVDF membrane (Immobilon-P, Millipore) was by transfer at 250 mA for 1 h in 5 mM CAPS (cyclohexylamino-propanesulfonic acid), pH 10.5, with 10% methanol, in a BioRad MiniTrans-Blot Cell. After transfer the bands were visualised by staining and destaining in 0.1 Coomassie in 50% methanol, and 10% acetic acid in 50% methanol, respectively, and were then excised and washed thoroughly in sterile distilled water. N-terminal amino acid analysis of proteins on the PVDF matrix used an Applied Biosystems 477A pulsed liquid phase sequencer. The amino acid sequence data was subsequently used to validate the identity of a sequenced ORF in a 4.9 kb BglII HaEPV genomic DNA clone (#36).

Fusion protein and antiserum. A 972 bp SspI fragment, comprising most of the coding region of the p50 spindle protein (fusolin) gene, was excised by restriction digestion and cloned into the pGex3X expression vector (Glutagene; Smith & Johnson, 1988); the recombinant plasmid was grown in *E. coli* (strain TG-1). Expression of the HaEPV p50-glutathione-S-transferase fusion product was induced by addition of IPTG (1 mM final concentration) to actively growing cells, and incubation for a further 3 h at 37° C. Bacteria were pelleted, resuspended in TEN (50 mM Tris, pH7.5; 2 mM EDTA; 100 mM NaCl) and lysed by incubation with lysozyme (0.2 mg/ml final concentration) for 30 min at 37°. Lysate was centrifuged (10000 g, 5 min) and the pellet resuspended in PBS. The highly insoluble fusion protein was partially purified by incubation of the lysate at 60° for 30 min in the presence of 30 mM urea and 0.2% SDS. The lysate mixture was then centrifuged as above, the pellet resuspended in PBS, denatured by boiling in SDS-PAGE sample loading buffer (Sambrook et al. 1989) and the protein separated on SDS-PAGE gels (4% stacking; 12.5% resolving). The fusion protein band was excised from the polyacrylamide gel, and rerun on an agarose gel (ProSieve, FMC). Protein was then eluted from excised agarose band and concentrated by ultrafiltration.

Purified fusion protein (about 5 μg) was mixed with Freunds adjuvant and injected subcutaneously into a rabbit. Booster injections used similar amounts of protein, and were administered 14, 28 and 35 days after the first injection; the latter boosters used the fusion protein in agarose gel matrix, thoroughly mixed with adjuvant. Antiserum was obtained from the rabbit on days 28 and 40.

For immunofluorescence studies suspensions of purified HaEPV spheroids and spindles were rinsed in PBS, washed twice in 0.05% Tween 20 in PBS, then incubated for 1 h at room temperature in 2% polyvinyl-pyrrolidone (PVP-40) in PBS. Preparations were washed twice more in 0.05% Tween 20, then incubated for 2 h in primary antibody (rabbit pre-immune serum, or anti-p50 fusion protein serum) diluted 1:500 in PBS. After washing three times, an equal volume of secondary antibody (FITC-conjugated goat and anti-rabbit IgG; Sigma F-9262) diluted 1:64 in PBS was added to the preparation and incubated overnight. The preparation was thoroughly rewashed in PBS, then mounted in 1% phenylenediamine in 50% glycerol in PBS. Examinations of fluorescence activity were made with a Wild Leitz confocal laser scanning microscope.

Proteins in HaEPV preparations. Electrophoresis of dissociated proteins from preparations containing HaEPV spheroids and spindles on Laemmli gels produced multiple bands of various intensities. When the same protein preparations were run on gels pre-treated with 20 mM glutathione, the profile was largely identical with the notable exception of a major band with apparent mobility of 50 kDa. Under standard Laemmli conditions a broad, diffuse band was observable in this region of the gel; with glutathione pretreatment a sharply defined p50 band replaced the diffuse one, and under these conditions was the most abundant protein present in our preparations. Other major bands identified in the preparations have been designated p120, p98, p87 and p21 on the basis of their apparent molecular weights.

N-terminal amino acid analysis of blotted p50 gave a sequence of His-Gly-Tyr-Met-Thr-Phe-Pro-Ile-(Ile/Ala)-Ala-Gln (SEQ ID NOS:5 & 6) for the first 11 residues. Attempts to define the N terminal amino acid composition of p120 by these methods were unsuccessful, apparently because the protein is blocked at that site.

Cloning and sequencing. Degenerate oligonucleotides were designed from the previously published sequence from *Chloristoneura biennis* EPV (Yuen et al. 1990) and synthesised on a Pharmacia LKB Gene Assembler Plus; oligonucleotide sequences were (5')GAATATGC(A/T)GC(A/T) TTAGCAGG(A/T/C)CC SEQ ID NO:9, and (5')ACA(A/G) TT(A/G)TA(A/G)AA(T/A)CCTTC(T/A)CC(T/C)AC SEQ ID NO:10. These oligos were used with standard polymerase chain reaction techniques (Sambrook et al. 1989) to generate an amplicon from purified HaEPV genomic DNA. That reaction used a total of 31 cycles; initial template denaturation was for 5 min at 94°, then the first 5 cycles used annealing, extension and denaturation temperatures of 42°, 72° and 94° respectively, all for 1.5 min. Remaining cycles were identical except that the annealing temperature was 50°, denaturation time was 1 min, and in the last cycle the extension step was for 5 min. The amplicon from the reaction served as template for synthesis of a random primed $^{32}$P-labelled DNA probe (Boehringer Mannheim). Southern blotting (Sambrook et al. 1989) was used to screen the fragments of interest in restriction enzyme digested HaEPV genomic DNA, and identified a 4.9 kb BglII fragment which was subsequently cloned into pTZ19R (Pharmacia).

This BglII fragment was subsequently cloned and sequenced (FIG. 1). Within this fragment an open reading frame which included the N-terminal amino acid sequence of p50 was found. The open reading frame consists of 1056 bases (including the termination codon), and is predicted to encode a 351 amino acid protein with a molecular weight of 40132 Da, and an isoelectric point of 5.87. The amino acid sequence identified as forming the N-terminal portion of p50 (see above) begins at amino acid 21 of the predicted protein, and is identical to the predicted sequence at 10 of the 11 residues. (Nucleotide sequence data from three independent genomic clones of the gene clearly indicate that an Arg is the tenth amino acid of the mature form of p50). This finding indicates that p50 is post-translationally modified; the truncated mature form of the protein has a predicted molecular weight of 37730 Da, an isoelectric point of 5.63, and contains 9 cysteine residues.

The 20 amino acid peptide apparently cleaved during maturation of p50 has a predicted molecular weight of 2420, an isoelectric point of 8.07, and has an hydrophobic central core. These features are consistent with those found in other viral peptides which act as leader sequences, and which direct movement of nascent proteins across intracellular membranes.

Comparison of HaEPV p50 amino acid sequence with others available in the data bank revealed major homology only with the *Choristoneura biennis* EPV (CbEPV) 50K protein (Yuen et al. 1990) and a related 34.8K protein of *Autographa californica* NPV (Viallard et al. 1990). Individual alignment of HaEPV p50 with each of those proteins using the Gap algorithm showed 63 and 42% identities respectively. Comparison of the predicted full length amino acid sequence of HaEPV p50 with the CbEPV 50K protein is shown in FIG. 2.

Each of the 9 cysteine residues in the mature form of HaEPV p50 has a corresponding Cys in CbEPV p50 (Yuen et al. 1990), and 6 of these 9 residues are also conserved in AcNPV p34.8. Conservation of the His-Gly-Tyr triad as the N-terminal end of the mature form of HaEPV p50 supports the previously suspected importance of this sequence (in combination with the amino acids immediately upstream) as a processing motif, and further suggests a likelihood of processing of AcNPV p34.8 at the analogous position (Vialard et al. 1990).

The 5' noncoding nucleotide sequence between the HaEPV p50 gene and the preceding putative open reading frame is 80 bases in length, 68 (85%) of which are A or T residues.

Comparison of the corresponding HaEPV and CbEPV noncoding regions using the Gap algorithm showed low (50%) nucleotide sequence homology (FIG. 3).

Western blotting of proteins present in purified preparations of HaEPV (containing both spheroids and spindle bodies) shows that the spindle protein, p50, is by far the most abundant protein present. Experiments on viral proteins in infected cells suggest that the spindle protein is also highly abundant in that milieu. Assuming then that the spindle protein gene is present at only one copy per EPV genome (which all indications would lead us to expect), the promoter of the p50 gene would appear to be the most active HaEPV viral promoter.

HaEPV p50 fusion protein and serological assays. The fusion protein containing HaEPV p50 and glutathione-S-transferase (GST) sequences had an expected molecular weight of about 64 kDa. Under SDS-PAGE conditions in which GST ran at its expected apparent molecular weight, the fusion protein migrated with an apparent molecular weight of 81 kDa.

On Western blots, pre-immune serum did not recognise blotted HaEPV proteins, but anti-p50 fusion serum showed a complex staining pattern. In addition to the expected recognition of p50, the antiserum reacted strongly against p98, and also against several higher molecular weight bands. These observations strongly suggest that p98 is a dimer of p50, and it then also seems likely that the higher molecular weight bands recognised by the antiserum are higher-order multimers of p50. The antiserum did not recognise p120 which is believed to be HaEPV spheroidin.

The pre-immune serum showed only very low levels of staining when used in immunofluorescence studies with preparations of HaEPV. In contrast, the anti-p50 fusion serum specifically bound to HaEPV spindle bodies, but showed no reactivity to spheroids. Confocal laser scanning microscopy clearly showed localisation of the anti-p50 fusion antibody to the spindle body, as visualised by fluorescence from a labelled second antibody.

It has also been found that a gene homologous to that which encodes HaEPV p50 is present in an EPV of the Australian melolonthine scarab species *Sericesthis nigrolineata*. Spindle bodies are produced by this virus.

Genomic DNA of SnEPV was prepared by disruption of spheroid bodies in thioglycollic acis and carbonate buffer, addition of one-tenth volume of Tris buffer (10 mM, pH 8.0) digestion with protease K(1 mg/ml, 4 hr at 37°), and dilution with 6 volumes of distilled water. A 4 microliter aliquot of this preparation was used as template in a PCR amplification, using the protocol and oligonucleotides detailed earlier. An amplicon of about 500 bp produced in that reaction was purified and cloned into pTZ19U (Pharmacia). The cloned amplicon was sequenced, and analysis of results clearly indicated the existence of homology between the amplicon sequence and that of the HaEPV spindle protein gene.

PCR protocols have also been used to detect the presence of an HaEPV gene with homology to the *Amsacta moorei* EPV and *Choristoneura biennis* EPV (CbEPV) spheroidin gene (sensu Hall and Moyer, 1991, 1993). Oligonucleotides RM58 and RM118 (Hall and Moyer, 1993) were synthesised and used with the HaEPV genomic DNA preparation described earlier, in the manner already described. An amplicon of about 1.1 kb was produced in this reaction; this is very close in size to the amplicon reported to be produced when the same oligos are used with CbEPV DNA as template (Hall and Moyer, 1993), and together with the known specificity of the PCR process, this provides strong evidence that the HaEPV-derived amplicon represents a portion of a spheroidin gene homologue present in the HaEPV genome.

Given the correspondence between the HaEPV genome and those of other entomopoxvirus genomes, demonstrated by results of the various protocols described above, it is very likely that a similar PCR-based methodology could be used to identify the presence of a thymidine kinase (TK) gene in the HaEPV genome. The presence of homologous TK genes in the genomes of AmEPV, CbEPV and *Choristoneura fumiferana* EPV has recently been demonstrated (Lytvyn et al. 1992).

Within the BglII fragment, an open reading frame coding for a putative 11.5 kDa protein was also identified. Analysis of DNA sequence upstream of the p11.5 ORF suggests that it is likely to be a strong promoter suitable for the expression of heterologous sequences.

EXAMPLE 2

Preparation of recombinant HaEPV (i) $G^+F^-$ (i.e. $GUS^+$spindle protein $(fusolin)^-$) HaEPV Recombinant $G^+F^-$ HaEPV was prepared as follows:

The 4.9 kb BglII HaEPV genomic fragment cloned in pTZ19R was used as the basis for construction of an EPV transfer vector. A section of that genomic fragment, approximately 700 bp in length, and delineated by the 5' BglII site and an internal EcoRI site, was deleted, leaving about 4.2 kb of HaEPV genomic DNA which included the sequence presented in FIG. 1. Site-directed mutagenesis was used to introduce a BamHI site between the upstream non-coding sequence and the coding region of the spindle protein gene. The transfer vector plasmid thus constructed was designated pEPAS3.

Further manipulation of pEPAS3 was achieved by use of a synthetic oligonucleotide (GATCTTAAATAGATCTATTTAA) (SEQ ID NO:11), which was self-annealed to give a dsDNA fragment with BamHI-compatible termini. This fragment was inserted into the BamHI site of pEPAS3, resulting in the incorporation of synthetic linker sequence, a vaccinia poxvirus consensus late promoter sequence (TAAAT), and a newly created BglII site, into that transfer vector. In the same process the pre-existing BamHI site of pEPAS3 was destroyed. This modified transfer vector was designated pEPAS3linker1.

The bacterial reported gene encoding the enzyme β-glucuronidase (GUS; Jefferson 1987) was inserted into the BglII site of pEPAS3linker1 to create pEPAS3linker1.GUS; in this construct an EcoRI site was introduced between the coding sequences of the GUS and spindle protein (fusolin) genes as a cloning artefact. The construct was multiplied in *E. coli* and subsequently purified by the Magic Maxiprep procedure (Promega). The purified DNA was transfected into *Heliothis zea* cells BCIRL-HZ-AM1 strain (McIntosh and Ignoffo, 1981) which had been infected by wild-type HaEPV 24 hours previously. Replication of HaEPV in these cells should be accompanied by the phenomenon of homologous recombination, resulting in the integration of a portion of the reporter (GUS)-containing construct into the genome of the virus. It was anticipated that the modified spindle protein promoter would drive expression of the GUS gene, and that the termination codon of the GUS gene would prevent co-expression of the spindle protein gene which was fused immediately downstream.

Figure 4A:
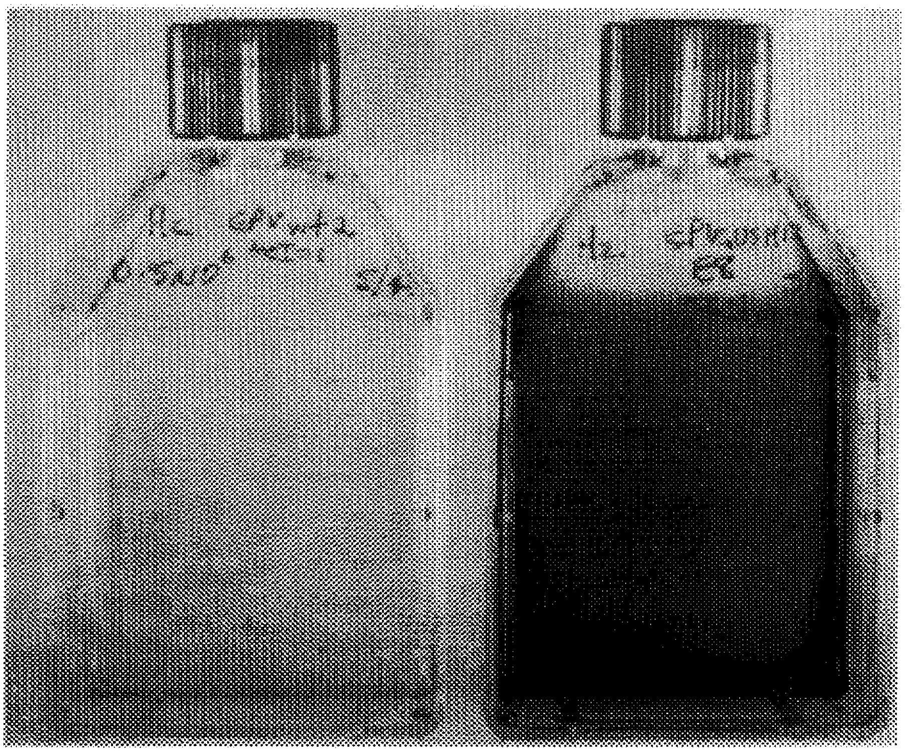
FIG. 4 (Parts A–B) (A): Demonstration of GUS activity in *H. zea* cells infected with wild-type *Heliothis armigera* entomopoxvirus (HaEPV; left) or isolated $G^+F^-$ recombinant HaEPV clone H12 (right).

Medium harvested from the infected/transfected *Heliothis zea* cells described above contained infectious particles of HaEPV, and was used to initiate further infection of other *H. zea* cells. Serial dilution of this medium to levels at which only one infectious particle was present in a given volume of inoculum allowed isolation of a $G^+F^-$ HaEPV recombinant, hereinafter designated as clone H12. Assessment of GUS activity of recombinant HaEPV's used the 5-bromo-4-chloro-3-indolyl glucurouide (X-GLU) substrate according to the protocol of Jefferson (1987b). FIG. 4(A) shows the results of this assay in whole cell infected with wild-type HaEPV (left flask) or with the $G^+F^-$ clone H12 HaEPV (right flask). It is clear that GUS activity is present only in the H12 HaEPV-infected cells. FIG. 5 shows results of the enzymatic assay for GUS enzyme activity in lysates of cells infected with the $G^+F^-$ clone H12 HaEPV, or wild-type HaEPV or mock-infected cells (i.e. no virus added) assessed by spectrophotometric analysis. It is clear that the GUS gene is expressed in the cells infected with the recombinant HaEPV, but that no such activity is associated with wild-type HaEPV, or the cells themselves.

A second recombinant $G^+F^-$ HaEPV was prepared as described above, except that the GUS reporter gene was cloned into the BamH1 site of transfer vector pEPAS3 to give pEPAS3:GUS. This vector was transfected into *H. zea* cells infected by wild-type HaEPV 24 hours earlier, again in expectation that $G^+F^-$ HaEPV recombinants with GUS gene expression driven by the wild-type spindle protein promoter, would be produced.

Figure 4B:
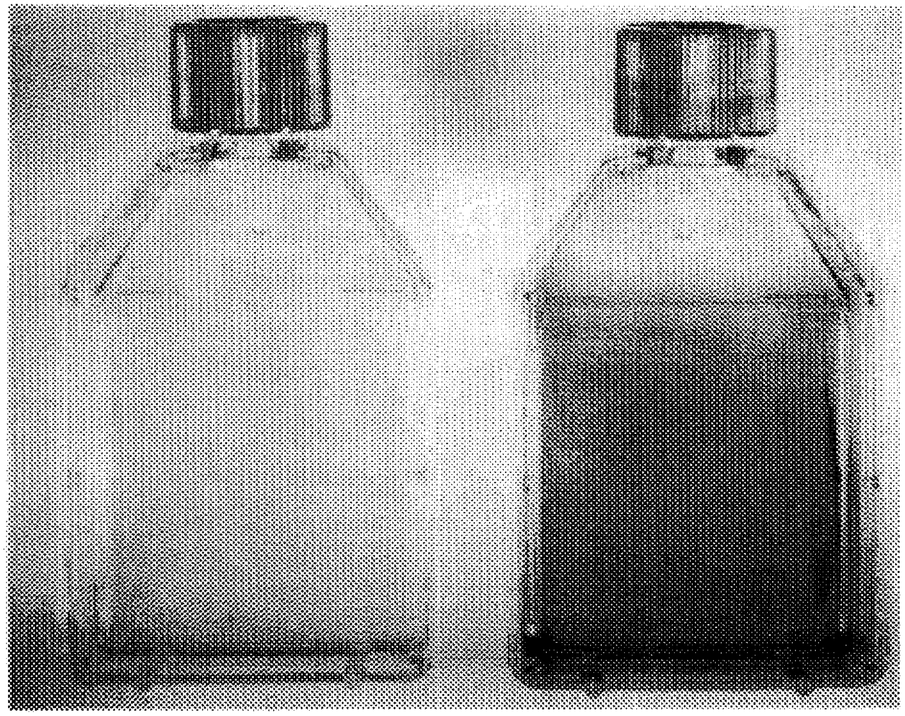

Assessment of GUS activity by the standard enzymatic assay again showed that the characteristic GUS-catalysed blue reaction product was present in cells subjected to the transfection/HaEPV infection protocol (FIG. 4(B) right flask), but not in cells infected with wild-type HaEPV (FIG. 4(B), left flask).

(ii) $G^+i$ HaEPV

Recombinant HaEPV possessing a copy of the GUS encoding sequence at the intergenic region (i) between p11.5 ORF and the spindle protein gene was prepared as follows:

Once again, a plasmid transfer vector was prepared based on the cloned 4.9 kb BglII HaEPV genomic segment.

Site-directed mutagenesis was used to introduce a BglII site into the intergenic region between the p11.5 ORF and the spindle protein coding sequence, in a manner designed to retain full activity of the spindle protein promoter. In this mutagenesis reaction the sequence ATATCT at positions −71 to −66 bases with respect to the spindle protein translation initiation codon (see FIG. 1) was changed to AGATCT; the resultant transfer vector construct was designated pEPAS4.

A DraI-EcoRI fragment from the pEPAS3:GUS construct, consisting of 49 bases of the wild-type spindle protein promoter sequence and the GUS coding sequence, was excised, made blunt-ended with Klenow fragment DNA polymerase, and cloned into the end-filled intergenic BglII site of pEPAS4. The transfer vector thus constructed was designated pEPAS4:GUS.

(iii) $Anti\text{-}neuraminidase^+F^-$ HaEPV

A recombinant HaEPV was prepared which expresses fused elements of the variable domains of heavy and light immunoglobulin chains of a mouse antibody directed against the neuraminidase protein of an influenza virus. This expression product is of potential use for the in vitro diagnosis of influenza. That protein has been additionally engineered to contain an octapeptide sequence which is recognised by a commercially available monoclonal antibody (anti-FLAG MS2 antibody; International Biotechnologies).

The gene (Malby, R. L. et al., 1993) encoding that protein was cloned into the BaHI site of pEPAS3, to give the transfer vector pEPAS3:NC10. Cotransfection of *H. zea* cells was as described above. Expression of the gene by recombination was demonstrated by detection of the protein product, using the anti-FLAG MS2 monoclonal antibody in a Western blot of proteins from recHaEPV-infected cells (FIG. 6).

(iv) $est^+F^-$ HaEPV

A recombinant HaEPV was prepared which expresses a juvenile hormone esterase gene of *Heliothis virescens* which has been mutated at position 201 to alter the serine residue to a glycine residue. This mutated protein has been shown to be highly insecticidal when expressed by a recombinant nuclear polyhedrosis virus and hence this recombinant HaEPV is considered to be a candidate for a useful viral insecticide.

This recombinant was prepared by cloning the mutated est gene into the BamHI site of pEPAS3 transfer vector, (Prof. B. B. Hammock, University of California, Davis, USA) and following the transfection/infection protocols described above.

REFERENCES

Arif, B. M. (1976). Isolation of an entomopoxvirus and characterisation of its DNA. Virology 69, 626–634.

Bilimoria, S. L. & Arif, B. M. (1979). Subunit protein and alkaline protease of entomopoxvirus spheroids. Virology 96, 596–603.

Buckner, C. H. & Cunningham, J. C. (1972). The effect of the poxvirus of the spruce budworm, *Choristoneura fumiferana* (Lepidoptera:Tortricidae), on mammals and birds. Can. Ent. 104, 1333–1342.

Erlandson, M. (1991). Protease activity associated with occlusion body preparations of an entomopoxvirus from *Melanoplus sanguinipes*. Journal of Invertebrate Pathology 57, 255–263.

Fernon, C. A. Vera, A. P., Crnov, R., Lai-Fook, J. & Dall, D. J. In vitro replication of *Heliothis armigera* EPV (in preparation).

Goodwin, R. H., Milner, R. J. & Beaton, C. D. (1991) Entomopoxvirinae. In Atlas of Invertebrate Viruses, Adams, J. R. & Bonami, J. R., eds. pp259–285. CRC Press, Boca Raton.

Hall, R. L. and Moyer, R. W. (1991) Identification, Cloning and Sequencing of a Fragment of *Amsacta moorei* Entomopoxvirus DNA Containing the Spheroidin Gene and Three Vaccinia Virus-Related Open Reading Frames. J. Virol. 65, 6516–6527.

Hall, R. L. and Moyer, R. W. (1993). Identification of an Amsacta spheroidin-like protein within the occlusion bodies of Choristoneura entomopoxviruses. Virology 192, 179–187.

Jefferson, R. A. (1987a) Plant Molecular Biology Reporter 5, 387–405.

Jefferson, R. A. (1987b). GUS Gene Fusion System User's Manual. Version 1.1 Cambridge, U.K.

Langridge, W. H. R. (1983). Detection of *Amsacta moorei* entomopoxvirus and vaccinia virus proteins in cell cultures restrictive for poxvirus multiplication. J. Invertebr. Pathol. 42, 77–82.

Lytvyn, V., Fortin, Y., Banville, M., Arif, B. and Richardson, C. (1992). Comparison of the thymidine kinase genes from three entomopoxviruses. J. Gen. Virol. 73, 3235–3240.

Malby, R. L., et al. PROTEINS: Structure, Function and Genetics, 16: 57–63, 1993.

McIntosh, A. H. and Ignoffo, C. M. (1981). Relication and infectivity of the single-embedded nuclear polyhedrosis virus, *Baculovirus heliothis*, in homologous cell lines. J. Invertebr. Pathol. 37, 258–264.

Sambrook, J. Fritsch, E. F. & Maniatis, T. (1989) Molecular Cloning: A Laboratory Manual. Second Edition, Cold Spring Harbour Laboratory Press, New York.

Smith, D. B. & Johnson, K. S. (1988). Single step purification of polypeptides expressed in *Escherichia coli* as fusions with glutathione-S-transferase. Gene 67, 31–40.

Towbin, H., Staehelin, T. & Gordon, J. (1979). Electrophoretic transfer of proteins from polyacrylamide gels to nitrocellulose sheets: procedure and some applications. Proceedings of the National Academy of Sciences, U.S.A. 76, 4350–4354.

Vailard, J. E., Yuen, L. & Richardson, C. D. (1990). Identification and characterisation of a baculovirus occulsion body glycoprotein which resembles spheroidin, and entomopoxvirus protein. J. Virol. 64, 5804–5811.

Yuen, L., Dionne, J., Arif, B. and Richardson, C. (1990). Identification and Sequencing of the Spheroidin Gene of *Choristoneura biennis* Entomopoxvirus. Virology 175, 427–433.

Other aspects of the present invention, and modifications and variations thereto, will become apparent to those skilled in the art on reading this specification, and all such other aspects and modifications and variations are to be considered as included within the scope of the present invention.

We claim:

1. A recombinant entomopoxvirus wherein heterologous DNA is located in the genome at the site of the spindle protein gene.

2. The recombinant entomopoxvirus according to claim 1 wherein the entomopoxvirus is selected from the group consisting of *Amsacta moorei* EPV, *Choristoneura biennis* EPV, *Heliothis armigera* EPV, *Choristoneura fumiferana* EPV, *Aphodius tasmaniae* EPV, *Dermolepida albohirtum* EPV, *Melolontha melolontha* EPV and *Sericesthis nigrolineata* EPV.

3. The recombinant entomopoxvirus according to claim 1 wherein the heterologous DNA comprises at least one gene encoding a substance deleterious to insects.

4. The recombinant entomopoxvirus according to claim 1 wherein the heterologous DNA comprises at least one gene encoding a desired biologically-active protein, polypeptide or peptide.

5. The recombinant entomopoxvirus according to claim 1 wherein the heterologous DNA is inserted in the viral genome via homologous recombination.

6. The recombinant entomopoxvirus according to claim 3 wherein the heterologous DNA encodes a substance selected from the group consisting of: *Bacillus thuringiensis* δ-toxin; insect neurohormones; proteins which interact with insect hormones; insecticidal compounds from wasps, insecticidal compounds from scorpion venom and insecticidal compounds of heterologous origin.

7. The recombinant entomopoxvirus according to claim 3 wherein the heterologous DNA encodes juvenile hormone esterase.

8. A method for controlling the proliferation of pest insects, comprising applying to an infested area the recombinant entomopoxvirus according to claim 3 optionally in admixture with an acceptable agricultural carrier.

9. The recombinant entomopoxvirus according to claim 4 where in the heterologous DNA encodes a substance selected from the group consisting of: IFN-α, IFN-β, IFN-δ, TPA, lymphotoxin, macrophage activating factor, insulin, epithelial cell growth factor, human growth factor, antibodies and antibody fragments.

10. The recombinant entomopoxvirus according to claim 4 wherein the heterologous DNA encodes fused elements of the variable domains of murine heavy and light immunoglobulin chains directed against neuraminidase of influenza virus.

11. The recombinant entomopoxvirus according to claim 4 wherein expression of heterologous DNA is driven by an entomopoxvirus promoter.

12. A method for producing a desired protein, polypeptide or peptide comprising infecting susceptible host cells with the recombinant entomopoxvirus according to claim 4.

13. The recombinant entomopoxvirus according to claim 11 wherein the entomopoxvirus promoter is the spindle protein promoter, spheroidin promoter or p11.5 ORF promoter from *Heliothis armigera* EPV.

14. A recombinant HaEPV wherein heterologous DNA is located in one or more non-essential regions of the genome selected from the group consisting of:

the site of p11.5 open reading frame (ORF);

the site of spindle protein gene; and the intergenic region between p11.5 ORF and the spindle protein gene.

15. A recombinant entomopoxvirus according to claim 14 wherein the heterologous DNA comprises at least one gene encoding a substance deleterious to insects.

16. The recombinant entomopoxvirus according to claim 14 wherein the heterologous DNA encodes a substances selected from the group consisting of IFN-α, IFN-β, IFN-δ, TPA, lymphotoxin, macrophage activating factor, insulin, epithelial cell growth factor, human growth factor, antibodies and antibody fragments.

17. The recombinant entomopoxvirus according to claim 14 wherein the heterologous DNA is inserted in the viral genome via homologous recombination.

18. A recombinant HaEPV wherein heterologous DNA is located at the site of p11.5 ORF of the genome.

19. A recombinant HaEPV wherein heterologous DNA is located at the site of the spindle protein encoding gene of the genome.

20. A recombinant HaEPV wherein heterologous DNA is located in the intergenic region of the genome between p11.5 ORF and at the site of the spindle protein encoding gene.

21. The recombinant entomopoxvirus according to claim 15 wherein the heterologous DNA encodes a substance selected from the group consisting of: *Bacillus thuringiensis* δ-toxin; insect neurohormones; proteins which interact with insect hormones; insecticidal compounds from wasps, insecticidal compounds from scorpion venom and insecticidal compounds of heterologous origin.

22. The recombinant entomopoxvirus according to claim 15 wherein the heterologous DNA encodes juvenile hormone esterase.

23. The recombinant entomopoxvirus according to claim 15 wherein the heterologous DNA comprises at least one gene encoding a desired biologically-active protein, polypeptide or peptide.

24. A method for controlling the proliferation of pest insects, comprising applying to an infested area the recombinant entomopoxvirus according to claim 15 optionally in admixture with an acceptable agricultural carrier.

25. The recombinant entomopoxvirus according to claim 23 wherein the heterologous DNA encodes fused elements of the variable domains of murine heavy and light immunoglobulin chains directed against neuraminidase of influenza virus.

26. The recombinant entomopoxvirus according to claim 23 wherein expression of the heterologous DNA is driven by an entomopoxvirus promoter.

27. The recombinant entomopoxvirus according to claim 23 wherein the entomopoxvirus promoter is the spindle protein promoter, spheroidin promoter or p11.5 ORF promoter from *Heliothis armigera* EPV.

28. A method for producing a desired protein, polypeptide or peptide comprising infecting susceptible host cells with the recombinant entomopoxvirus according to claim 23.

29. An isolated DNA molecule comprising a nucleotide sequence encoding *Heliothis armigera* entomopoxvirus spindle protein.

30. An isolated DNA molecule comprising a nucleotide sequence consisting of nucleotide 443 to nucleotide 1498 in FIG. 1.

31. An isolated DNA molecule comprising a nucleotide sequence encoding *Heliothis armigera* EPV p11.5 ORF.

32. An isolated DNA molecule comprising a nucleotide sequence consisting of nucleotide 57 to nucleotide 362 in FIG. 1.

33. An isolated DNA molecule comprising a nucleotide sequence encoding the intergenic region that lies between p11.5 ORF and at the site of the spindle protein gene of the *Heliothis armigera* entomopoxvirus genome.

34. An isolated DNA molecule comprising a nucleotide sequence consisting of nucleotide 363 to nucleotide 442 in FIG. 1.

35. An isolated DNA molecule comprising a nucleotide sequence encoding an entomopoxvirus spindle protein promoter or functional portion thereof.

36. The isolated DNA molecule according to claim 35 wherein the spindle protein promoter is derived from *Heliothis armigera* entomopoxvirus.

37. An isolated DNA molecule comprising a nucleotide sequence encoding an entomopoxvirus p11.5 ORF promoter or functional portion thereof.

38. The isolated DNA molecule according to claim 37 wherein the p11.5 ORF promoter is derived from *Heliothis armigera* entomopoxvirus.

39. An isolated DNA molecule comprising a nucleotide sequence consisting of nucleotide 1 to nucleotide 56 in FIG. 1.

40. An isolated DNA molecule encoding a fused promoter element comprising an entomopoxvirus spindle protein promoter sequence and a vaccinia consensus late promoter sequence.

* * * * *